(12) United States Patent
Zondlo et al.

(10) Patent No.: US 8,551,723 B2
(45) Date of Patent: Oct. 8, 2013

(54) TYROSINE KINASE-INDUCIBLE DOMAINS

(75) Inventors: Neal J. Zondlo, Newark, DE (US); Susan Carr Zondlo, Newark, DE (US); Feng Gao, Tianjin (CN)

(73) Assignee: University of Delaware, Newark, DE (US)

( * ) Notice: Subject to any disclaimer, the term of this patent is extended or adjusted under 35 U.S.C. 154(b) by 101 days.

(21) Appl. No.: 13/078,494

(22) Filed: Apr. 1, 2011

(65) Prior Publication Data

US 2011/0244498 A1    Oct. 6, 2011

Related U.S. Application Data

(60) Provisional application No. 61/320,578, filed on Apr. 2, 2010.

(51) Int. Cl.
*C12Q 1/48* (2006.01)
*C07K 7/08* (2006.01)

(52) U.S. Cl.
USPC ............................. 435/15; 530/326; 530/327

(58) Field of Classification Search
None
See application file for complete search history.

(56) References Cited

U.S. PATENT DOCUMENTS 7,816,102 B2   10/2010   Zondlo

FOREIGN PATENT DOCUMENTS

WO    WO 03087152 A1 * 10/2003

OTHER PUBLICATIONS

Manning et al, Science, 2002, 298,: 1912-1934.
Lawrence et al., Chembiochem 2007, 8(4),: 373-378.
Ting et al., Proc. National Acad. Sci. 2001, 98, (26), : 15003-15008.
Kurokawa, et al., J. Biol. Chem., 2001, 276, (33), : 31305-31310.
Shults, et al., Nature Methods, 2005, 2(4): 277-83. Epub Mar. 23, 2005.
Wang, et al., J. Am. Chem. Soc. 2006, 128, : 1808-1809.
Szilak, et al., Protein Sci. 1997, 6, : 1273-1283.
Signarvic, et al., J. Mol. Biol. 2003, 334, : 1-12.
Atkinson, et al., D. Chem. Comm. 2004, pp. 438-439.
Atkinson, et al., Org. Biomol. Chem., 2006, 4, : 3166-3171.
Siedlecka, et al., Proc. Natl. Acad. Sci. USA, 1999, 96, : 903-908.
Macmanus, et al., J. Biol. Chem., 1990, 265, (18), : 10358-10366.
Turk, B. E., Curr. Opin. Chem. Biol. 2008, 12(1), : 4-10.
Placzek, et al., Anal. Biochem., 2010, 397(1), : 73-78.
Aurora, et al., Protein Sci., 1998, 7, : 21-38.
Tonks, N. K., Nat. Rev. Mol. Cell. Biol., 2006, 7, : 833-846.
Ostman, et al., Nat. Rev. Cancer, 2006, 6, : 307-320.
Lukovic, et al., Angew Chem Int. Ed. Engl. 2009; 48(37): 6828-6831.

\* cited by examiner

*Primary Examiner* — Cecilia J Tsang
*Assistant Examiner* — Randall L Beane
(74) *Attorney, Agent, or Firm* — RatnerPrestia (57) ABSTRACT

The present invention relates to a tyrosine kinase-inducible domain (pKID) and uses thereof. An isolated polypeptide comprising the pKID, and an isolated polynucleotide comprising a nucleic acid sequence encoding the pKID are provided. Also provided are methods for determining tyrosine kinase and/or phosphatase activity in a sample and for identifying an agent that inhibits a tyrosine kinase or phosphatase using a polypeptide comprising the pKID.

3 Claims, 4 Drawing Sheets
(4 of 4 Drawing Sheet(s) Filed in Color)

| | |
|---|---|
| *EF Hand-E12* | DKNADGYIDAAEK |
| *pKID-pTyr11* | DKNADGWIDAYAK |
| *pKID-pTyr15a* | DKNADGWIDAAAAKYAK |
| *pKID-pTyr15b* | DKDGDGWISPAAAKYAK |
| *pKID-Abl* | DKDADGWEAIYAAPFAK |
| *EF control-E11* | DKNADGWIDAEAK |
| *pKID-pTyr12* | DKNADGYIDAAYK |

SEQUENCE LISTING

```
<160> NUMBER OF SEQ ID NOS: 14

<210> SEQ ID NO 1
<211> LENGTH: 13
<212> TYPE: PRT
<213> ORGANISM: Artificial Sequence
<220> FEATURE:
<223> OTHER INFORMATION: Synthetic

<400> SEQUENCE: 1

Asp Lys Asn Ala Asp Gly Trp Ile Asp Ala Tyr Ala Lys
1               5                   10

<210> SEQ ID NO 2
<211> LENGTH: 17
```

```
<212> TYPE: PRT
<213> ORGANISM: Artificial Sequence
<220> FEATURE:
<223> OTHER INFORMATION: Synthetic

<400> SEQUENCE: 2

Asp Lys Asp Ala Asp Gly Trp Glu Ala Ile Tyr Ala Ala Pro Phe Ala
1               5                   10                  15

Lys

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Asp Lys Asn Ala Asp Gly Trp Ile Asp Thr Tyr Thr Ala Phe Ala Ala
1               5                   10                  15

Lys

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Asp Lys Asn Ala Asp Gly Trp Val Asp Gly Tyr Val Lys Pro Gln Ile
1               5                   10                  15

Lys

<210> SEQ ID NO 5
<211> LENGTH: 16
<212> TYPE: PRT
<213> ORGANISM: Artificial Sequence
<220> FEATURE:
<223> OTHER INFORMATION: Synthetic

<400> SEQUENCE: 5

Asp Lys Asp Ala Asp Gly Trp Glu Asp Ile Tyr Phe Ala Phe Lys Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Asp Lys Asp Ala Asp Gly Trp Glu Gly Thr Tyr Gly Val Val Lys
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Synthetic

<400> SEQUENCE: 7

Asp Lys Asn Ala Asp Gly Trp Ile Asp Ala Ala Ala Ala Lys Tyr Ala
1               5                   10                  15
```

Lys

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8

Asp Lys Asp Gly Asp Gly Trp Ile Ser Pro Ala Ala Ala Lys Tyr Ala
1               5                   10                  15

Lys

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Asp Lys Asp Ala Asp Gly Trp Glu Gly Thr Tyr Gly Val Val Lys
1               5                   10                  15

<210> SEQ ID NO 10
<211> LENGTH: 18
<212> TYPE: PRT
<213> ORGANISM: Artificial Sequence
<220> FEATURE:
<223> OTHER INFORMATION: Synthetic

<400> SEQUENCE: 10

Asp Lys Asp Ala Asp Gly Trp Ile Ser Ala Lys Gln Val Glu Tyr Leu
1               5                   10                  15

Asp Leu

<210> SEQ ID NO 11
<211> LENGTH: 16
<212> TYPE: PRT
<213> ORGANISM: Artificial Sequence
<220> FEATURE:
<223> OTHER INFORMATION: Synthetic

<400> SEQUENCE: 11

Asp Lys Asp Ala Asp Gly Trp Glu Phe Ile Tyr Gly Glu Ile Asp Ala
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: Synthetic

<400> SEQUENCE: 12

Asp Lys Asp Ala Asp Gly Trp Glu His Val Tyr Ser Phe Pro Asn Lys
1               5                   10                  15

Lys

<210> SEQ ID NO 13
<211> LENGTH: 25
<212> TYPE: PRT
<213> ORGANISM: Artificial Sequence
<220> FEATURE:

```
<223> OTHER INFORMATION: Synthetic

<400> SEQUENCE: 13

Ala Tyr Thr Asp Thr Ile Asp Thr Trp Ser Thr Pro Glu Gln Leu Ala
1               5                   10                  15

Lys Glu Leu Leu Gln Glu His Gly Ile
            20                  25

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Gly Arg Arg Arg Arg Arg Arg Arg Arg Pro Pro Pro Gly Gly Cys
1               5                   10                  15
```

TYROSINE KINASE-INDUCIBLE DOMAINS

CROSS-REFERENCE TO RELATED APPLICATION

This application claims the benefit of U.S. Provisional Application No. 61/320,578, filed Apr. 2, 2010, the contents of which are incorporated in their entireties.

SEQUENCE LISTING

The Sequence Listing, which is a part of the present disclosure, includes a computer file "SequenceListingUOD320US.txt," which is 4 KB and was generated by U.S. Patent & Trademark Office Patent In Version 3.5 software on Mar. 31, 2011. The subject matter of the Sequence Listing is incorporated herein by reference in its entirety.

FIELD OF THE INVENTION

The invention relates generally to a tyrosine kinase-inducible domain as well as methods for determining tyrosine kinase or phosphatase activity and methods for identifying a tyrosine kinase or phosphatase inhibitor.

BACKGROUND OF THE INVENTION

Tyrosine kinases are critical mediators of intracellular signaling that are misregulated in numerous cancers. Tyrosine kinase inhibitors are therefore emerging as important therapeutics in oncology. In addition, tyrosine kinase signaling is broadly implicated as important in other diseases, including diabetes, heart disease, and viral and bacterial infectivity. The importance of tyrosine phosphorylation in disease has inspired the development of numerous approaches to interrogate tyrosine kinase-mediated signaling.

Tyrosine phosphatases have critical roles in the temporal dynamics of cell signaling via their role in dephosphorylating kinases and kinase substrates. Changes in tyrosine phosphatase activities are associated with numerous human diseases, including diabetes, obesity, inflammatory diseases, and some cancers. Accordingly, inhibitors of tyrosine phosphatases have received increasing attention as possible therapeutics.

Several groups have developed encodable sensor systems for tyrosine kinases Src, Abl, and the EGF receptor. (Ting et al., 2001, *Proc. Natl. Acad. Sci. USA* 98:15003-15008.) These systems are based on changes in fluorescence resonance energy transfer and involve four components: cyan fluorescent protein, a kinase recognition site, a binding module for the phosphorylated (kinase-activated) protein, and yellow fluorescent protein. These systems appear to be reasonably generally applicable to different protein kinases if a binding module is known or can be developed for a kinase recognition site. However, the changes in fluorescence on phosphorylation are relatively modest for these systems, reducing sensitivity to small changes. In addition, the large size (greater than 50 kD) of the structures limits the potential applications of the system, particularly their employment as protein tags, (1) due to the possibility of steric interference by the sensor system if it were used as a protein tag; (2) by making full biophysical characterization of the system difficult; and (3) by increasing the development time for new kinase sensors. These encodable systems are in general not well suited to solution assays due to their size.

Sensitive fluorescence-based sensing systems have been developed for protein kinase activity, demonstrating as much as 9-fold fluorescence difference between non-phosphorylated and phosphorylated protein. (Lawrence and Wang, 2007, *ChemBioChem* 8:373-378; Wang and Lawrence, 2005, *Am. Chem. Soc.* 127:7684-7685; Wang et al., 2006, *J. Am. Chem. Soc.* 128:1808-1809,) These probes can allow real-time analysis of kinase activity and thus hold great promise, and are clearly far more convenient than previously employed radioassays or immunoassays of protein kinase activity. However, these sensors have the limitation that they incorporate external fluorophores and thus cannot be expressed. Similarly, kinase probes have been demonstrated for the activities of multiple kinases having as much as 10-fold differences in fluorescence between phosphorylated and non-phosphorylated peptide. (Shults and Imperiali, 2003, *J. Am. Chem. Soc.* 125:14248-14249; Vazquez et al., 2003, *J. Am. Chem. Soc.* 125:10150-10151; Shults et al., 2005, *Nature Methods* 2:277-283.) However, these systems are based on an unnatural amino acid and thus also cannot be expressed in vivo. In addition, the unnatural amino acids employed are not commercially available. Moreover, in most cases these systems are generally limited to kinase recognition sequences that are either N-terminal or C-terminal to the tyrosine residue that is phosphorylated. However, the specificity in protein phosphorylation by protein kinases usually involves residues both N-terminal and C-terminal to the phosphorylated residue. In addition, in many signaling cascades, kinase specificity is dependent on scaffolding proteins and protein-binding domains, requiring the localization of a sensor as a tag (ideally small) on substrate proteins. While synthetic constructs have been developed combining recognition sequences and a targeting protein, the absence of encodability limits the applications of these systems. (Placzek et al., 2010, *Analytical Biochem.* 397:73-78; Lukovic et al., 2009, *Angewandte Chemie-International Edition* 48:6828-6831.)

A protein kinase-inducible domain (pKID) was previously designed to become structured and bind lanthanides when phosphorylated on serine or threonine. (Balakrishnan and Zondlo, 2006, *J. Am. Chem. Soc.* 128:5590-5591; U.S. Pat. No. 7,816,102.) In that design, phosphoserine or phosphothreonine mimicked a structurally important Glu residue, generating phosphorylation-dependent EF-hand peptides. In the design of a protein dependent on tyrosine phosphorylation, the size differences between phosphotyrosine and Glu precludes an approach involving direct mimicry of Glu by phosphotyrosine.

To date, no system combines large changes in fluorescence with the ability to express the kinase sensor as a protein tag. Given the importance of tyrosine kinase and phosphatase activities in human health and diseases, there remains a need for new tools to assess changes in tyrosine kinase and/or phosphatase activity as a function of a cell state or disease.

SUMMARY OF THE INVENTION

The present invention relates to a tyrosine kinase-inducible domain and its use for determining tyrosine kinase and/or phosphatase activity in a sample, and for identifying an agent that inhibits a tyrosine kinase or phosphatase.

A first aspect of the present invention provides an isolated polypeptide comprising a tyrosine kinase-inducible domain (pKID). The pKID domain comprises an amino acid sequence having formula (I):

$$DKX^1X^2DGWX^3X^4X^5X^6X^7X^8X^9X^{10} \qquad (I)$$

wherein $X^1$ is D or N;
$X^2$ is A or G;
$X^3$, $X^4$ and $X^5$ are each an amino acid; and
$X^6$ is Y while $X^7$, $X^8$, $X^9$ and $X^{10}$ are each an optionally present amino acid; or $X^{10}$ is Y while $X^6$, $X^7$, $X^8$ and $X^9$ are each an amino acid.

$X^3$-$X^{10}$ may comprise a recognition sequence of one or more tyrosine kinases or tyrosine phosphatases.

The pKID may or may not be phosphorylated.

The pKID may further comprise a tyrosine kinase recognition sequence. Suitable tyrosine kinases include Abl, EGFR, ErbB2, Fyn, FAK, VEGFR, InR, Src, Lyn, Hck, JAK, or c-Met kinases. The pKID may comprise an amino acid sequence selected from the group consisting of SEQ ID NOs: 1-12.

The pKID may further comprise a tyrosine phosphatase recognition sequence. Suitable tyrosine phosphatases include YOP, PTP1B, cdc25, and SHP1 phosphatases, and include both tyrosine phosphatases and dual specificity phosphatases.

A second aspect of the present invention provides an isolated polynucleotide comprising a nucleic acid sequence encoding the tyrosine kinase-inducible domain (pKID).

A third aspect of the present invention provides a method for determining the activity of one or more tyrosine kinases and/or one or more tyrosine phosphatases in a sample. The method comprises (a) providing a polypeptide comprising the tyrosine kinase-inducible domain (pKID); (b) incubating the sample in the presence of the polypeptide under conditions that permit production of luminescence; and (c) detecting the luminescence. An increase in the detected luminescence after the incubation as compared with that before the incubation indicates that the one or more tyrosine kinases are active in the sample; while a decrease in the detected luminescence after the incubation as compared with that before the incubation indicates that the one or more tyrosine phosphatases are active in the sample.

The method may further comprise quantitating the luminescence. The method may also further comprise adding a tyrosine kinase or phosphatase to the sample. When the method is used primarily to detect tyrosine kinase activity, the polypeptide in step (a) is preferably not phosphorylated; and the pKID may comprise a recognition sequence for the one or more tyrosine kinases. Preferably, the pKID comprises an amino acid sequence selected from the group consisting of SEQ ID NOs: 1-12. When the method is used primarily to detect tyrosine phosphatase activity, the polypeptide in step (a) is preferably phosphorylated; and the pKID may comprise a recognition sequence for the one or more tyrosine phosphatases.

The sample may comprise cells, cell extracts, a tissue or tissue extracts. The sample may be obtained from a subject. The subject may be a mammal, preferably a human. The subject may have suffered or may be suspected to suffer a disease. Examples of the diseases include cancers, diabetes, Alzheimer's disease, heart disease, viral infection (e.g., HIV infection, and pox infection), and bacterial infection (e.g., E. coli). The cancer may be chronic myelogenous leukemia, lung cancer, colon cancer, breast cancer, or metastatic cancer.

A fourth aspect of the present invention provides a method for identifying for an agent that inhibits a tyrosine kinase. The method comprises (a) providing a polypeptide comprising the tyrosine kinase-inducible domain (pKID); (b) incubating the polypeptide in the presence of the tyrosine kinase and the agent under conditions that permit production of luminescence; and (c) detecting the luminescence. A decrease in the detected luminescence in the presence of the agent as compared with that in the absence of the agent indicates that the agent inhibits the tyrosine kinase. The polypeptide in step (a) is preferably not phosphorylated. The pKID preferably comprises a recognition sequence for the tyrosine kinase. The method may be further used to quantitate the detected luminescence.

A fifth aspect of the present invention provides a method for identifying for an agent that inhibits a tyrosine phosphatase. The method comprises (a) providing a polypeptide comprising the tyrosine kinase-inducible domain (pKID); (b) incubating the polypeptide in the presence of the tyrosine phosphatase and the agent under conditions that permit production of luminescence; and (c) detecting the luminescence. An increase in the detected luminescence in the presence of the agent as compared with that in the absence of the agent indicates that the agent inhibits the tyrosine phosphatase. The polypeptide in step (a) is preferably phosphorylated. The pKID preferably comprises a recognition sequence for the tyrosine phosphatase. The method may further comprise quantitating the detected luminescence.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The present invention is based on the discovery of a protein tyrosine kinase-inducible domain (pKID), a small, genetically encodable protein motif whose structure is dependent on its tyrosine phosphorylation state. The pKID comprises residues that bind metal and produces luminescence when phosphorylated by a tyrosine kinase.

The term "tyrosine kinase" as used herein refers to an enzyme that is capable of phosphorylate a tyrosine residue in a peptide, polypeptide or protein substrate. One or more tyrosine kinases can specifically recognize and bind a specific sequence in a substrate, and phosphorylate a tyrosine residue in or near the tyrosine kinase recognition sequence. Examples of tyrosine kinases include Abl, EGFR, ErbB2, Fyn, FAK, VEGFR, InR, Src, Lyn, Hck, JAK, or c-Met kinases.

The term "tyrosine phosphatase" as used herein refers to an enzyme that is capable of dephosphorylate a phosphotyrosine residue in a peptide, polypeptide or protein. One or more tyrosine phosphatases can specifically recognize and bind a specific sequence in a substrate, and dephosphorylate a phosphotyrosine residue in or near the tyrosine phosphatase recognition sequence. In some cases, a tyrosine kinase recognition sequence is also a tyrosine phosphatase recognition sequence. Tyrosine phosphatases include both classical tyrosine phosphatases as well as dual specificity phosphatases. For example, tyrosine phosphatases may be YOP, PTP1B, cdc25, or SHP1 phosphatase.

According to one aspect of the invention, tyrosine kinase-inducible domains are provided. In particular, the tyrosine kinase-inducible domains are designed based on EF-hand loops in which a structurally important Glu12 residue is replaced by tyrosine at residue 11 or at residue 15 of the protein. A "structurally important" residue of a peptide plays an important role in the secondary, tertiary, and/or quaternary structure of the peptide. EF Hand proteins (e.g., calmodulin) bind calcium and contain a critical Glu at position 12 that binds metal in a bidentate manner. Upon calcium binding, EF hand proteins undergo a significant conformational change to a well-folded helix-loop-helix structure. Because of the similar electronics and ionic radii of calcium and lanthanides, EF hands effectively coordinate lanthanides, thereby endowing the EF hand with the luminescent, magnetic, and hydrolytic properties of lanthanides.

Elimination of Glu12 by replacement with a phosphotyrosine at position 11 or position 15 (along the same helical face) allows the phosphotyrosine to structurally mimic the Glu and bind metal. The non-phosphorylated residue does not bind metal. Notably, EF Hand binds, for example, terbium with terbium luminescence (fluorescence) dependent on both the presence of a nearby donor chromophore (Trp, within 10 Angstroms) and reduced access to water. Thus, the non-phosphorylated peptide does not bind metal and is non-luminescent, or weakly binds metal and is weakly luminescent, whereas the phosphorylated peptide binds metal and shows strong luminescence. Critically, residues near the metal-binding Glu are not critical and may be replaced by residues of a kinase-recognition sequence, generating a protein motif whose structure and luminescence are fully dependent on phosphorylation.

According to the present invention, a tyrosine kinase-inducible domain (pKID) comprises amino acid residues that are in contact with a metal via, for example, side chain or a main chain carbonyl. Where the expression of the pKID in cells is desired, the pKID consists entirely of canonical amino acids to enable its use as a genetically encoded tyrosine phosphorylation-dependent protein tag and as a building block in the design of larger tyrosine phosphorylation-dependent protein architectures. The pKID disclosed according to the present invention can be readily produced via any expression system as known in the art. The effectiveness of the pKID can be optimized using technology known in the field.

In one embodiment, an isolated polypeptide comprising a tyrosine kinase-inducible domain (pKID) is provided. The pKID comprises an amino acid sequence having the following formula:

$$DKX^1X^2DGWX^3X^4X^5X^6X^7X^8X^9X^{10} \qquad (I)$$

wherein X$^1$ is D or N;
X$^2$ is A or G;
X$^3$, X$^4$ and X$^5$ are each an amino acid; and
X$^6$ is Y while X$^7$, X$^8$, X$^9$ and X$^{10}$ are each an optionally present amino acid; or X$^{10}$ is Y while X$^6$, X$^7$, X$^8$ and X$^9$ are each an amino acid.

For formula (I), standard polypeptide abbreviations for amino acid residues are used, as shown in Table 1.

TABLE 1

| Abbreviation of Amino Acid Residues | | |
|---|---|---|
| 1-Letter Code | 3-Letter Code | Amino Acid |
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The tyrosine kinase-inducible domain (pKID) may or may not be phosphorylated by a tyrosine kinase. A non-phosphorylated pKID may be used for determining tyrosine kinase activity in a sample and for identifying a tyrosine kinase inhibitor or agent. A phosphorylated pKID may be used for determining tyrosine phosphatase activity in a sample or for screening a tyrosine phosphatase inhibitor or agent. The approach may be used to interpret changes in solution or in a cell as a result of stimuli or addition of agents. Also, the approach may be used to detect the simultaneous and competing activities of tyrosine kinases and tyrosine phosphatases, in the absence or presence of stimuli or of chemical modulators or inhibitors. In addition, the approach may be used to monitor the activities of multiple tyrosine kinases and tyrosine phosphatases that act on a single substrate. Further, the approach may be used to detect the activities of unknown tyrosine kinases and phosphatases that are known to phosphorylate and dephosphorylate a given protein sequence incorporated in the pKID.

The tyrosine kinase-inducible domains according to the present invention may bind metals, including terbium, europium, gadolinium, and other lanthanide metals, and can be used for imaging of kinase activity and/or phosphatase activity by nuclear magnetic resonance or magnetic resonance imaging.

Upon tyrosine phosphorylation, the pKID exhibits a structural change. The phosphorylated pKID binds a metal (e.g., terbium) and produces luminescence under suitable conditions (e.g., conditions that permit production of luminescence). An increase in the luminescence may be used as an indication of the presence of tyrosine kinase activity.

The tyrosine kinase-inducible domain (pKID) may further comprise a recognition sequence for a tyrosine kinase. Such a tyrosine kinase recognition sequence provides the pKID with a specificity for the tyrosine kinase. Suitable tyrosine kinases include Abl, EGFR, ErbB2, Fyn, FAK, VEGFR, InR, Src, Lyn, Hck, JAK, and c-Met kinases. The pKID may comprise any of the following amino acid sequences:

```
pKID-pTyr11     DKNADGWIDAYAK       SEQ ID NO: 1 pKID-Abl        DKDADGWEAIYAAPFAK   SEQ ID NO: 2 pKID-Abl-auto   DKNADGWIDTYTAFAAK   SEQ ID NO: 3 pKID-EGFR       DKNADGWVDGYVKPQIK   SEQ ID NO: 4 pKID-ErbB2      DKDADGWEDIYFAFKK    SEQ ID NO: 5 pKID-Fyn        DKDADGWEGTYGVVK     SEQ ID NO: 6 pKID-pTyr15a    DKNADGWIDAAAAKYAK   SEQ ID NO: 7 pKID-pTyr15b    DKDGDGWISPAAAKYAK   SEQ ID NO: 8 pKID-Src        DKDADGWEGTYGVVK     SEQ ID NO: 9 pKID-EGFR-15    DKDADGWISAKQVEYLDL  SEQ ID NO: 10 pKID-PTK        DKDADGWEFIYGEIDA    SEQ ID NO: 11 pKID-FAK        DKDADGWEHVYSFPNKK   SEQ ID NO: 12
```

The pKID may also comprise a sequence that is at least 70%, 80%, 90%, 95%, 95% identical to any of SEQ ID NO: 1-12.

The pKID may further comprise a recognition sequence for the tyrosine phosphatase. The incorporation of such a recognition sequence makes a phosphorylated pKID suspect to the tyrosine phosphatase. Such a phosphorylated pKID may be used to determine the activity of the tyrosine phosphatase in a sample and to identify an agent that inhibits the tyrosine phosphatase. Suitable tyrosine phosphatases include, for example, YOP, PTP1B, cdc25, and SHP1 phosphatases, and include both tyrosine phosphatases and dual specificity phosphatases.

In addition to EF hand domains, a tyrosine kinase-inducible domain ("inducible domain") may be derived from another protein so long as such a domain contains a structurally important or significant glutamic acid residue. For example, a zinc finger domain, Zif268, can be redesigned to bind terbium or other lanthanide metals, with metal binding by glutamic acid residues at positions 18 and 22 in lanthanide FIG. 6 (LF6) having an amino acid sequence of AYT-DTIDTWSTPEQLAKELLQEHGI (SEQ ID NO: 13) as described in *ChemBioChem* 2010, 11, 1738-1747, the contents of which are incorporated in their entireties. Using a phosphotyrosine at residue 17 or at residue 21 may mimic structurally critical Glu18 or Glu22 residues in the zinc finger domain, and result in a tyrosine kinase and/or phosphatase inducible domain.

An isolated polypeptide comprising the tyrosine kinase-inducible domain (pKID) can be made using any technique known in the art. In particular, the polypeptide may be a tagged protein comprising a protein of interest and the pKID. The presence of the tagged protein in a sample (e.g., cell extracts, cells or a tissue) may be determined by detecting luminescence upon phosphorylation or dephosphorylation of the pKID in the tagged protein. The tagged protein may be used to detect protein kinase and/or protein phosphatase activity in a sample, including the detection of protein kinase and/or protein phosphatase activities in subcellular locations.

Also, an isolated polynucleotide comprising a nucleic acid sequence encoding the pKID can be produced using any technique known in the art. The polynucleotide may comprise a nucleic acid sequence encoding a pKID tagged protein using any technique known in the art. Further, an isolated polynucleotide comprising a nucleic acid complementary to the nucleic acid sequence which encodes the pKID can be generated using any technique known in the art.

When the pKID is phosphorylated by a tyrosine kinase, the production of luminescence is increased under suitable conditions (e.g., conditions that permit production of luminescence). However, an inhibitor of the tyrosine kinase can reduce or eliminate the luminescence production.

On the other hand, when the pKID is dephosphorylated by a tyrosine phosphatase, the production of luminescence is decreased under suitable conditions (i.e., conditions that permit production of luminescence). Also, an inhibitor of the tyrosine phosphatase can increase or restore the luminescence production.

According to another aspect of the invention, a method for determining tyrosine kinase activity in a sample comprising a tyrosine kinase is provided. The method comprises (a) providing a polypeptide comprising a tyrosine kinase-inducible domain (pKID); (b) incubating the sample in the presence of the polypeptide under conditions that permit production of luminescence; and (c) detecting the luminescence. An increase in the detected luminescence after the incubation as compared with that before the incubation indicates that the tyrosine kinase is active in the sample. An increase in the detected luminescence in the presence of the polypeptide as compared with that in the absence of the polypeptide or in the absence of the tyrosine kinase may also indicate that the tyrosine kinase is active in the sample. The method may further comprise quantitating the detected luminescence. The increase may be at least 20%, 25%, 50%, 100%, or 2, 5, 10, 15 or 20 folds, preferably at least 2 folds. The magnitude of the increase in the detected luminescence may be used to indicate the level of the tyrosine kinase activity.

The term "conditions that permit production of luminescence" refers to conditions under which, upon incubation, the sample exhibits luminescence. Such conditions include, but are not limited to, the presence of a nearby donor chromophore (Trp, Tyr, phosphotyrosine, or other fluorophores, within 10 Angstroms of the metal) and reduced access to water. The luminescence may be quantified to determine the quantity of the tyrosine kinase activity in the sample.

In the method for determining tyrosine kinase activity, the polypeptide in step (a) is preferably not phosphorylated. The pKID may further comprise a recognition sequence for the tyrosine kinase so that the polypeptide may be specifically phosphorylated by the tyrosine kinase. The pKID may comprise an amino acid sequence selected from the group consisting of SEQ ID NOs: 1-12.

The sample may comprise a solution. It may also comprise cells, cell extracts, a tissue, or tissue extracts. The polypeptide may be introduced into the cells by any method as known in the art, e.g., by transfection, injection and liposomal delivery.

The sample may be obtained from a subject. The subject may be a mammal, preferably a human. The subject may have suffered or is suspected to suffer a disease. Examples of the diseases include cancer (e.g., chronic myelogenous leukemia, lung cancer, colon cancer, breast cancer, metastatic cancer), diabetes, heart disease, viral infection (e.g., HIV infection, pox infection), and bacterial infection (e.g., E. coli).

Where assessing (e.g., detecting imaging, or quantitating) tyrosine kinase or phosphatase activity in cells (e.g., fixed cells and live cells) is desired, a polypeptide comprising the tyrosine kinase-inducible domain (pKID) may be conjugated with a cell-penetrating polypeptide (CPP), and introduced into the cells via, for example, incubation. The CPP may be conjugated to the pKID via a disulfide or via other covalent bonds. An exemplary CPP sequence is GRRRRRRRRPP-PGGC (SEQ ID NO: 14).

A method for determining tyrosine phosphatase activity in a sample comprising a tyrosine phosphatase is also provided. The method comprises (a) providing a polypeptide comprising a tyrosine kinase-inducible domain (pKID); (b) incubating the sample in the presence of the polypeptide under conditions that permit production of luminescence; and (c) detecting the luminescence. A decrease in the detected luminescence after the incubation as compared with that before the incubation indicates that the tyrosine phosphatase is active in the sample. A decrease in the detected luminescence in the presence of the polypeptide as compared with that in the absence of the polypeptide or in the absence of the tyrosine phosphatase may also indicate that the tyrosine phosphatase is active in the sample. The polypeptide in step (a) is preferably phosphorylated. The decrease may be at least 20%, 25%, 50%, 100%, or 2, 5, 10, 15, or 20 folds, preferably at least 2 folds. The magnitude of the decrease in the detected luminescence may be used to indicate the level of the tyrosine phosphatase activity.

In the method for determining tyrosine phosphatase activity, the polypeptide in step (a) is preferably phosphorylated. The pKID may further comprise a recognition sequence for the tyrosine phosphatase so that the polypeptide may be specifically dephosphorylated by the tyrosine phosphatase. In addition, the polypeptide may be a substrate for one of several known or unknown tyrosine phosphatases or dual-specificity phosphatases.

A method for determining the activity of one or more tyrosine kinases and/or one or more tyrosine phosphatases in a sample is further provided. The method comprises (a) providing a polypeptide comprising the tyrosine kinase-inducible domain (pKID); (b) incubating the sample in the presence of the polypeptide under conditions that permit production of luminescence; and (c) detecting the luminescence. An increase in the detected luminescence after the incubation as compared with that before the incubation indicates that the one or more tyrosine kinases are active in the sample; while a decrease in the detected luminescence in the presence of the polypeptide as compared with that in the absence of the polypeptide indicates that the one or more tyrosine phosphatases are active in the sample. The method may further comprise quantitating the luminescence.

In a method for determining the activity of one or more tyrosine kinases and/or one or more tyrosine phosphatases in a sample according to the present invention, the sample may comprise a mixture of one or more tyrosine kinases and one or more tyrosine phosphatases. The method may further comprise adding a tyrosine kinase or phosphatase to the sample. When the method is used primarily to detect tyrosine kinase activity, the polypeptide in step (a) is preferably not phosphorylated; and the pKID may comprise a recognition sequence for the one or more tyrosine kinases. Preferably, the pKID comprises an amino acid sequence selected from the group consisting of SEQ ID NOs: 1-12. When the method is used primarily to detect tyrosine phosphatase activity, the polypeptide in step (a) is preferably phosphorylated; and the pKID may comprise a recognition sequence for the one or more tyrosine phosphatases.

According to yet another aspect of the invention, a method for identifying an agent that inhibits tyrosine kinase activity is provided. The method comprises (a) providing a polypeptide comprising the tyrosine kinase-inducible domain (pKID); (b) incubating the polypeptide in the presence of the tyrosine kinase and the agent under conditions that permit production of luminescence; and (c) detecting the luminescence. A decrease in the detected luminescence in the presence of the agent as compared with that in the absence of the agent indicates that the agent inhibits the tyrosine kinase. The decrease may be at least 20%, 50%, 100%, or 2, 5, 10, 15, or 20 folds, preferably at least 2 folds. The polypeptide in step (a) is preferably not phosphorylated. Preferably, the pKID further comprises a recognition sequence for the tyrosine kinase. The pKID may alternatively include a protein sequence known to be phosphorylated by one or more unidentified tyrosine kinases. The method may further comprise quantitating the detected luminescence. The magnitude of the decrease in the detected luminescence may be used to indicate the level of the agent's tyrosine kinase inhibition effect.

A method for identifying an agent that inhibits tyrosine phosphatase activity is further provided. The method comprises (a) providing a polypeptide comprising the tyrosine kinase-inducible domain (pKID); (b) incubating the polypeptide in the presence of the tyrosine phosphatase and the agent under conditions that permit production of luminescence; and (c) detecting the luminescence. An increase in the detected luminescence in the presence of the agent as compared with that in the absence of the agent indicates that the agent inhibits the tyrosine phosphatase. The increase may be at least 20%, 50%, 100%, or 2, 5, 10, 15, or 20 folds, preferably at least 2 folds. The polypeptide in step (a) is preferably phosphorylated. Preferably, the pKID further comprises a recognition sequence for the tyrosine phosphatase. The pKID may alternatively include a protein sequence known to be de-phosphorylated by one or more unidentified tyrosine phosphatases. The method may further comprise quantitating the detected luminescence. The magnitude of the increase in the detected luminescence may be used to indicate the agent's level of the tyrosine phosphatase inhibition effect.

Example 1

Design of Encodable Tyrosine Kinase-Inducible Domains

Tyrosine kinase-inducible domain peptides were designed and evaluated for detection of tyrosine kinase activity by terbium luminescence. The materials, methods and results of this experiment are described in Zondlo et al., *J. Am. Chem. Soc.* 2010, 132(16):5619-21 and its Supporting Information, the contents of each of which are hereby incorporated in their entireties.

The tyrosine kinase-inducible domain peptides bind terbium(III) in a phosphorylation-dependent manner, showing strong terbium luminescence when phosphorylated but weak terbium luminescence when not phosphorylated. Lanthanide binding was confirmed by NMR. A tyrosine kinase-inducible domain peptide, pKID-Abl, was designed to incorporate a recognition sequence of the Abl kinase. Incubation of pKID-Abl with the Abl kinase resulted in a large increase in terbium luminescence. This increase in luminescence was abolished when the pKID-Abl and the Abl kinase were incubated with the Abl kinase inhibitor Gleevec®. In addition, incubation of phosphorylated pKID-Abl with the tyrosine phosphatase YOP resulted in a large reduction in terbium luminescence. pKID-Abl was employed as a fluorescent sensor of Abl tyrosine kinase activity in HeLa cell extracts, exhibiting low luminescence with extracts from serum-starved cells and increased luminescence using extracts from EGF-treated cells. These results indicate that tyrosine kinase-inducible domains may be used as sensors of tyrosine kinase and tyrosine phosphatase activity and in the detection of tyrosine kinase inhibitors.

Figure 1:
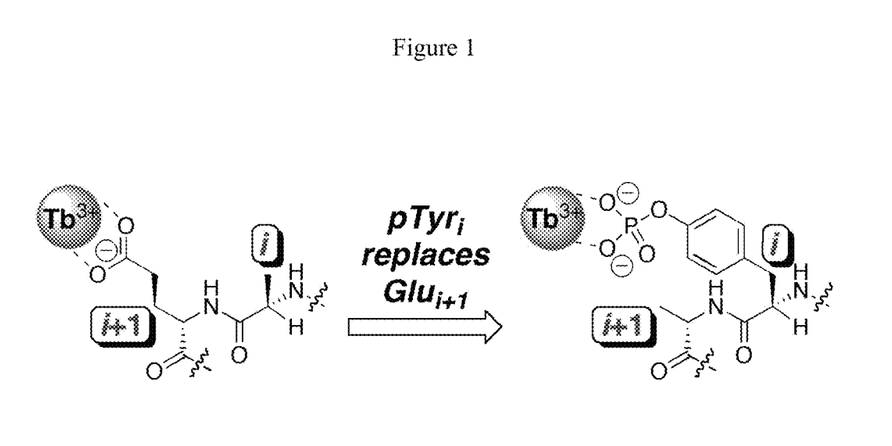
FIG. 1 shows a design of a protein motif dependent on tyrosine phosphorylation. Phosphotyrosine (pTyr) at the i position mimics Glu at the i+1 position. Nonphosphorylated tyrosine is expected to be a poor Glu mimic.

The length of the phosphotyrosine side chain suggested a structure-based approach to phosphorylation-dependent protein design. The conserved $Glu_{12}$ of EF-hand proteins is located within an α-helix. In α-helices and other compact conformations, the side chains of sequential residues may interact to stabilize protein structure (i.e., i/i+1 interactions). A sufficiently long side chain at the i residue could functionally replace an interaction of the i+1 residue (FIG. 1). Accordingly, a tyrosine kinase-inducible domain peptide has been designed to have a phosphotyrosine residue (i position, residue 11 of an EF-hand) to replicate the electrostatic and Lewis base properties of a structurally important Glu residue at the i+1 position (residue 12).

Figure 2:
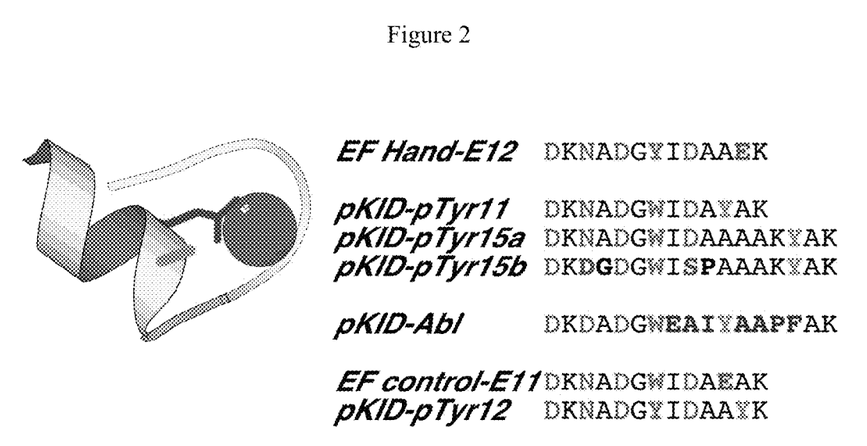
FIG. 2 shows the structure of an EF hand (1c11), with $Glu_{12}$ (red) and the $C_\alpha$-$C_\beta$ bond of residue 11 (green) emphasized (left), and the sequences of a canonical EF hand, tyrosine kinase-inducible domain peptides, and control peptides (right). Residues in red contact metal via the side chain; $Glu_{12}$ binds metal in a bidentate manner; residue 9 (Asp or Ser) contacts metal via a water-mediated contact in EF-hand proteins. $Trp_7$ (magenta) contacts metal via the main chain carbonyl and is a sensitizer for terbium luminescence. Residues in green are sites of phosphorylation. Residues in blue represent an Abl kinase recognition sequence.
Figure 3:
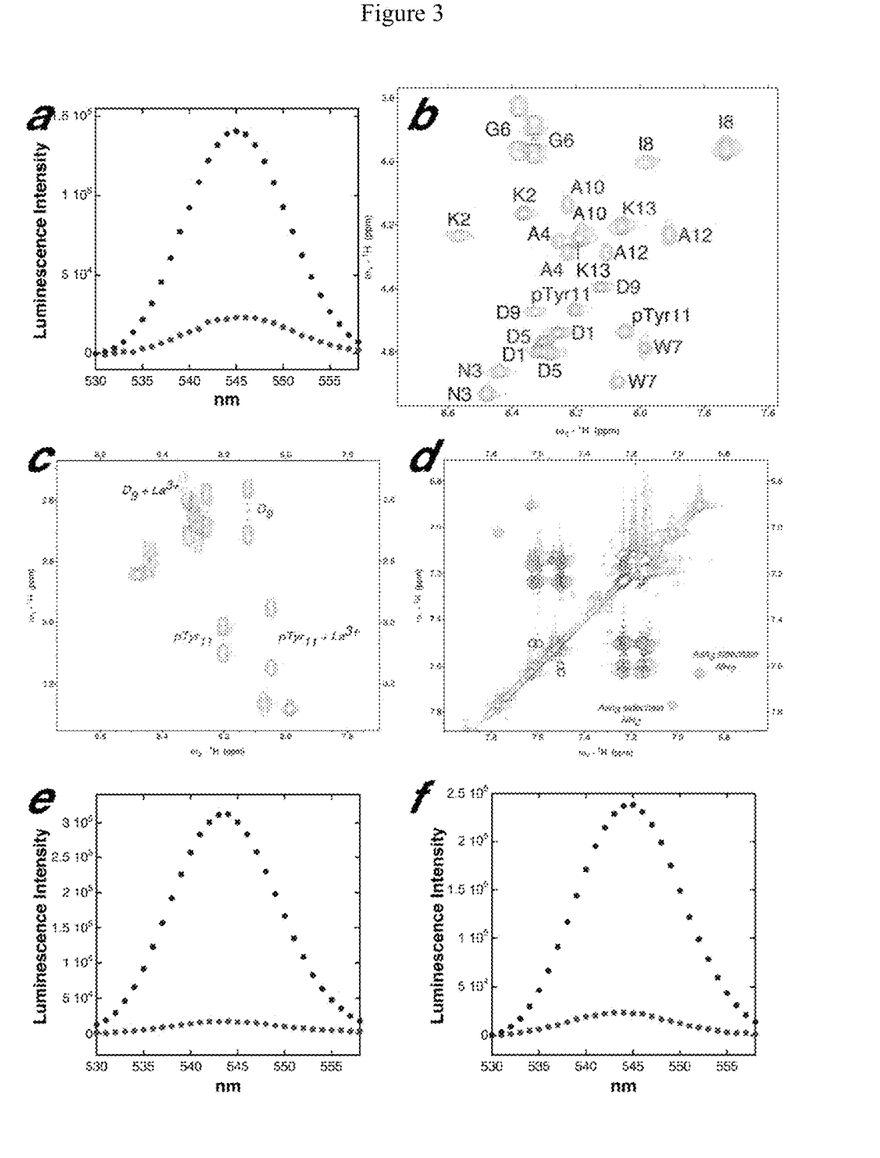
FIGS. 3a, 3e and 3f show the luminescence spectra of 10 µM non-phosphorylated (red) and phosphorylated (blue) (a) pKID-pTyr11, (e) pKID-pTyr15a, and (f) pKID-pTyr15b, in the presence of (a, f) 20 µM $Tb^{3+}$ or (e) 80 µM $Tb^{3+}$. Experiments were conducted in water with 10 mM HEPES (pH 7.8) and 100 mM NaCl with excitation at 280 nm. At the indicated $Tb^{3+}$ concentrations, the phosphorylated peptides exhibited (a) 6.4-fold, (e) 17.6-fold, and (f) 10.1-fold greater luminescence than the non-phosphorylated peptides, respectively. The fold luminescence differentiation between non-phosphorylated and phosphorylated peptides depends on the relative $Tb^{3+}$ affinities of the peptides and on the $Tb^{3+}$ concentration.
FIGS. 3b, 3c, and 3d show the TOCSY spectra of phosphorylated pKID-pTyr11 in the absence (red) and presence (blue) of $La^{3+}$ indicating metal-induced peptide folding: (b) $H^N$—$H_\alpha$ region; (c) $H^N$—$H_\beta$ region; (d) aromatic region.

To test this approach, the model peptide pKID-pTyr11 was synthesized, consisting of a consensus EF-hand sequence with $Glu_{12}$ replaced by Ala; Tyr at residue 11; and $Trp_7$ to sensitize terbium luminescence (FIG. 2). pKID-pTyr11 exhibited phosphorylation-dependent $Tb^{3+}$ binding and luminescence: non-phosphorylated pKID-pTyr11 was nearly non-luminescent in conditions where phosphorylated pKID-pTyr11 exhibited strong terbium luminescence (FIG. 3a). Phosphorylated pKID-pTyr11 bound $Tb^{3+}$ with 35-fold greater affinity than did the non-phosphorylated peptide ($K_d$=54±9 µM versus $K_d$=1900±280 µM). Notably, the $Tb^{3+}$ binding of phosphorylated pKID-pTyr11 was identical in the presence of 100 µM $Ca^{2+}$ and 2 mM $Mg^{2+}$, indicating compatibility of the design with competitive solution conditions. Phosphorylated pKID-pTyr11 bound $Tb^{3+}$ with similar affinity to the EF Hand consensus peptide (EF Hand-E12) with Glu at residue 12 ($K_d$=88±8 µM), indicating that phosphotyrosine at the i residue effectively mimics Glu at the i+1 residue. Notably, phosphorylated pKID-pTyr11 bound $Tb^{3+}$ with far greater affinity than a control peptide with Glu at residue 11 ($K_d$=1820±140 µM), indicating that a negatively charged amino acid at residue 11 is not sufficient for the observed metal binding and that the length of the phosphotyrosine side chain is necessary for binding from residue 11. In addition, phosphorylated pKID-pTyr11 also exhibited greater $Tb^{3+}$ affinity than a peptide with phosphotyrosine at residue 12 ($K_d$=209±32 µM), consistent with the design.

The binding of phosphorylated pKID-pTyr11 was further characterized by NMR experiments, which revealed a significant structural change for all residues upon addition of the diamagnetic lanthanide $La^{3+}$, including chemical shift changes in key metal-binding residues, consistent with the design (FIG. 3b-d). Notably, the $Ile_8$ $H^N$ main chain and the $Asn_3$ side chain amides, both of which are conjugated to carbonyls that contact metal in EF-hand proteins, as well as the $Asp_9$ and $pTyr_{11}$ $H_\beta$ protons, exhibited significant $La^{3+}$-dependent changes in their chemical shifts. Of particular note is the large increase in dispersion of the diastereotopic $Gly_6$ and $pTyr_{11}$ $H_\beta$ chemical shifts, consistent with adoption of an organized structure on addition of $La^{3+}$. In sum, these data are consistent with side chain organization among EF Hand $Ca^{2+}$-binding residues upon metal binding.

Tyrosine kinase recognition sites incorporate residues both N-terminal and C-terminal to tyrosine that provide kinase specificity. In order to develop an approach that might broadly accommodate sequence substitution, to be generally compatible with diverse tyrosine kinase recognition sequences, two additional peptides, pKID-pTyr15a and pKID-pTyr15b, were synthesized (FIG. 2). In these peptides, Tyr is translated forward one α-helical turn, to residue 15. Due to the geometry of an α-helix, phosphotyrosine at residue 15 should project toward the EF-hand metal-binding site. pKID-pTyr15a and pKID-pTyr15b differ in the identity of residues 3 and 9 in the metal coordination sphere, and in the conformational preferences of non-coordinating residues 4 and 10. Modulation of the electrostatics of residues 3 and 9 of the coordination sphere can dramatically impact $Tb^{3+}$ affinity and luminescence in EF Hand peptides.

Both pKID-pTyr15a and pKID-pTyr15b showed phosphorylation-dependent luminescence, indicating that phosphotyrosine$_{15}$ was critical for protein structure (FIG. 3e-f). Of these peptides, phosphorylated pKID-pTyr15b exhibited greater $Tb^{3+}$ affinity ($K_d$=47±5 µM, compared to $K_d$=217±21 µM for pKID-pTyr15a) and a larger difference in $Tb^{3+}$ affinity between the phosphorylated and non-phosphorylated peptides, while phosphorylated pKID-pTyr15a exhibited modestly greater maximum luminescence at $Tb^{3+}$ saturation. These data indicate that the N-terminal sequence in kinase-inducible domain peptides may be used to tune their structural and luminescence characteristics.

To examine the compatibility of tyrosine kinase-inducible domain peptides with a complex kinase recognition sequence, the peptide pKID-Abl was synthesized (FIG. 2). pKID-Abl incorporates the critical kinase recognition residues from the optimized Abl substrate peptide Abltide. As observed previously with model peptides, pKID-Abl exhibited strong phosphorylation-dependent $Tb^{3+}$ luminescence (FIG. 4a; $K_d$=26±6 µM phosphorylated pKID-Abl, versus $K_d$=411±38 µM for non-phosphorylated pKID-Abl), suggesting its potential utility as a sensor of Abl kinase activity.

Incubation of non-phosphorylated pKID-Abl with Abl kinase resulted in a significant increase in terbium luminescence (FIG. 4b), indicating that pKID-Abl may be used as a sensor of Abl kinase activity. Luminescent detection of kinase inhibition by the Abl inhibitor Gleevec® was also readily observed using pKID-Abl, suggesting that kinase-inducible domain peptides are also effective for screening protein kinase inhibitors.

Figure 4:
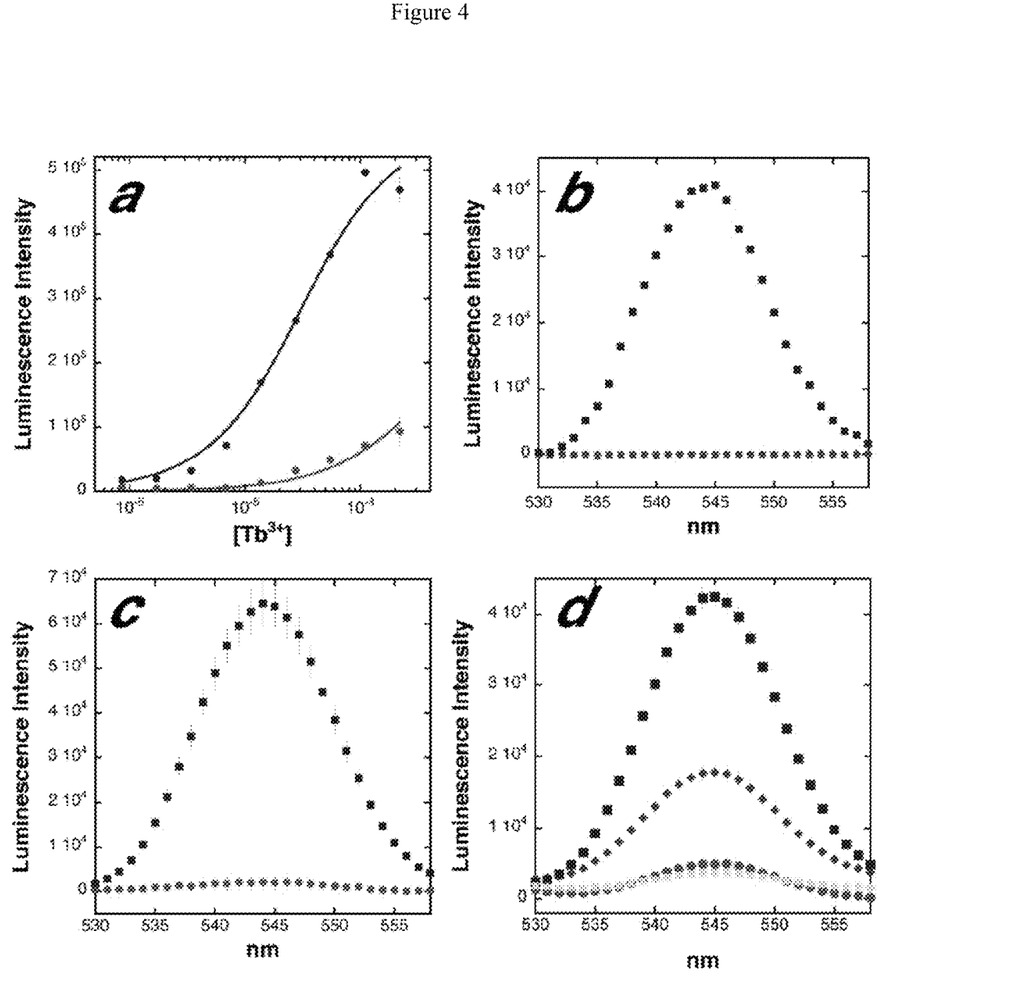
FIG. 4a shows the $Tb^{3+}$ binding isotherm of 10 µM non-phosphorylated (red) and phosphorylated (blue) pKID-Abl in 10 mM HEPES (pH 7.5), 100 mM NaCl, and 2 mM $MgCl_2$.
FIG. 4b shows luminescence spectra of 30 µM pKID-Abl with 50 µM $Tb^{3+}$ (final concentrations) after incubation in the absence of Abl kinase (red squares), in the presence of Abl kinase (blue circles; 62% phosphorylated), or in the presence of Abl kinase and Gleevec® (green triangles; <5% phosphorylated); reaction mixtures were incubated for 30 min at 37° C. in buffer containing 10 mM HEPES pH 7.5, 100 mM NaCl, 2 mM MgCl$_2$, 2 mM DTT, and 400 µM ATP, followed by addition of Tb$^{3+}$.
FIG. 4c shows luminescence spectra of 10 µM phosphorylated pKID-Abl with 20 µM Tb$^{3+}$ prior to (blue) and 1 min after (red) incubation with the tyrosine phosphatase YOP.
FIG. 4d shows measurement of EGF-induced Abl kinase activity using pKID-Abl in HeLa cell extracts via Tb$^{3+}$ luminescence. Red circles, luminescence of cell extracts, from untreated cells, in the presence of non-phosphorylated pKID-Abl (t$_0$); green diamonds, luminescence of cell extracts, from untreated cells, after incubation with pKID-Abl (28% phosphorylation); blue squares, luminescence of cell extracts, from cells treated with EGF, after incubation with pKID-Abl (69% phosphorylation); triangles, cell extracts, from untreated (yellow) and EGF-treated (cyan) cells, in the absence of pKID-Abl. The data indicate a 2.4-fold increase in luminescence observed in extracts from the EGF-stimulated cells over those from non-stimulated cells, and an 8.6-fold increase in luminescence for pKID-Abl in extracts from EGF-stimulated cells over extracts with non-phosphorylated pKID-Abl. The extent of phosphorylation was determined by HPLC analysis. Error bars indicate standard error.

In order to examine the potential of a tyrosine kinase-inducible domain peptide to detect tyrosine phosphatase activity, phosphorylated pKID-Abl was incubated with the tyrosine phosphatase YOP. pKID-Abl was an effective sensor of tyrosine phosphatase activity, with a large and rapid reduction in terbium luminescence observed due to dephosphorylation of $pTyr_{11}$ by YOP (FIG. 4c).

Finally, in order to examine the use of pKID-Abl to analyze changes in cellular kinase activity, pKID-Abl was incubated with untreated HeLa cell extracts and with HeLa cell extracts stimulated with epidermal growth factor (EGF), which induces Abl kinase activity (FIG. 4d). The large dynamic range of tyrosine kinase-inducible domains resulted in strong differentiation of treated and untreated cells and the ready identification of induced cellular tyrosine kinase activity. More generally, these results suggest compatibility of kinase-inducible domain peptides with highly complex solution conditions. In sum, these results indicate that tyrosine kinase-inducible domains may be broadly applied toward the luminescent detection of tyrosine kinase and tyrosine phosphatase activities.

Materials

Amino acids and resin for peptide synthesis were purchased from Novabiochem. HBTU was purchased from Senn Chemicals. Diisopropylethylamine (DIPEA) was purchased from Aldrich. Dimethylformamide (DMF), methylene chloride, and trifluoroacetic acid (TFA) were purchased from Acros. Other compounds were purchased from Acros unless otherwise indicated. Peptide concentrations were determined by UV/VIS for non-phosphorylated peptides based on tryptophan and tyrosine absorbance ($\epsilon$=6980 $M^{-1}$ $cm^{-1}$ at 280 nm in water) and for phosphorylated peptides based on tryptophan and phosphotyrosine absorbance ($\epsilon$=6350 $M^{-1}$ $cm^{-1}$ at 280 nm in water, using $\epsilon$=650 $M^{-1}$ $cm^{-1}$ for phosphotyrosine) on a PerkinElmer Lambda 25 spectrometer. Chemical phosphorylation reactions were performed in capped disposable fritted columns (Image Molding). Terbium(III) chloride stocks were freshly prepared from the hexahydrate salts (Aldrich).

Peptide Synthesis and Characterization

Peptides were synthesized via standard Fmoc solid phase peptide synthesis on a CEM Liberty microwave peptide synthesizer or on a Rainin PS3 peptide synthesizer. All peptides were synthesized using Fmoc-Tyr(2-Cl-Trt)-OH at the site of tyrosine phosphorylation. After synthesis, peptides were acetylated using 10% acetic anhydride in pyridine, with the exception of pKID-Abl, which was not acetylated. For site-selective phosphorylation of tyrosine, the trityl group was selectively removed from each peptide with 2% TFA and 5% triethylsilane (TES) in $CH_2Cl_2$ (3×1 min). Phosphorylation was performed under nitrogen by addition to 50 mg resin of tetrazole (1.35 mmol; 3 mL of 3% tetrazole in acetonitrile) (Transgenomics) and O,O-dibenzyl-N,N-diisopropylphosphoramidite (500 μL, 1.52 mmol) (Fluka), and the mixture allowed to react for 3 h with gentle mixing on a Barnstead-Thermoline Labquake rotary shaker. The resin was washed with DMF (3×) and $CH_2Cl_2$ (3×). Oxidation was performed with t-butyl hydroperoxide (3 mL of a 3 M solution in $CH_2Cl_2$) and allowed to react with mixing for 30 min. Peptides were cleaved and side chains deprotected for 2.5 to 3 h with a solution of 40 μL thioanisole, 40 μL ethanedithiol, 40 μL phenol, 40 μL $H_2O$, and 1.5 mL TFA. TFA was evaporated with nitrogen, the peptides were precipitated with ether, and the peptides dissolved in $H_2O$.

Peptides were purified by reverse phase HPLC (Vydac semipreparative C18, 10×250 mm, 5 μm particle size, 300 Å pore). Peptides were purified to homogeneity using a linear gradient of 0-40% buffer B (80% MeCN, 20% $H_2O$, 0.05% TFA) in buffer A (98% $H_2O$, 2% MeCN, 0.06% TFA) for 60 min for the peptides non-phosphorylated pKID-pTyr15b, phosphorylated pKID-pTyr15b, non-phosphorylated pKID-Abl, and phosphorylated pKID-Abl. A 0-35% gradient of Buffer B in Buffer A over 60 min was used for the peptide non-phosphorylated pKID-pTyr11. A 0-30% gradient of Buffer B in Buffer A over 60 min was used for the peptides phosphorylated pKID-pTyr11, non-phosphorylated pKID-pTyr12, phosphorylated pKID-pTyr12, EF Control-E11, and EF Hand-E12. A 0-60% gradient of Buffer B in Buffer A over 60 min was used for non-phosphorylated pKID-pTyr15a and phosphorylated pKID-pTyr15a. Peptide purity was indicated by the presence of a single peak on reinjection on analytical HPLC (Microsorb MV C18, 4.6×250 mm, 3-5 μm particle, 100 Å pore). Peptide identity was characterized by ESI-MS in positive ion mode (except EF Hand-E12, which was characterized in negative ion mode) on an LCQ Advantage (Finnigan) mass spectrometer (Table S1). Retention times for the peptides: non-phosphorylated pKID-pTyr11, $t_R$ 51.3 min; phosphorylated pKID-pTyr11, $t_R$ 47.3 min; non-phosphorylated pKID-pTyr15a, $t_R$ 34.7 min; phosphorylated pKID-pTyr15a, $t_R$ 31.4 min; non-phosphorylated pKID-pTyr15b, $t_R$ 44.3 min; phosphorylated pKID-pTyr15b, $t_R$ 40.9 min; non-phosphorylated pKID-Abl, $t_R$ 59.1 min; phosphorylated pKID-Abl, $t_R$ 54.2 min; non-phosphorylated pKID-pTyr12, $t_R$ 51.8 min; phosphorylated pKID-pTyr12, $t_R$ 45.4 min; EF Control-E11, $t_R$ 47.5 min; and EF Hand-E12, $t_R$ 50.9 min.

TABLE 2

Characterization data for the non-phosphorylated and phosphorylated peptides

| Peptide | Sequence | Calculated mass | Mass observed |
|---|---|---|---|
| non-phosphorylated pKID-pTyr11 | Ac-DKNADGWIDAYAK-NH$_2$ | 1507.6 | 1509.6 $[M + 2H]^{2+}$ |
| phosphorylated pKID-pTyr11 | Ac-DKNADGWIDApYAK-NH$_2$ | 1586.1 | 1589.4 $[M + 2H]^{2+}$ |
| non-phosphorylated pKID-pTyr15a | Ac-DKNADGWIDAAAAKYAK-NH$_2$ | 1849.0 | 1850.6 $[M + 2H]^{2+}$ |
| phosphorylated pKID-pTyr15a | Ac-DKNADGWIDAAAAKpYAK-NH$_2$ | 1928.0 | 1930.2 $[M + 2H]^{2+}$ |

TABLE 2-continued

Characterization data for the non-phosphorylated and phosphorylated peptides

| Peptide | Sequence | Calculated mass | Mass observed |
|---|---|---|---|
| non-phosphorylated pKID-pTyr15b | Ac-DKDGDGWISPAAAKYAK-NH$_2$ | 1834.1 | 1835.6 [M + 2H]$^{2+}$ |
| phosphorylated pKID-pTyr15b | Ac-DKDGDGWISPAAAKpYAK-NH$_2$ | 1913.1 | 1916.4 [M + 2H]$^{2+}$ |
| non-phosphorylated pKID-Abl | Ac-DKDADGWEAIYAAPFAK-NH$_2$ | 1909.1 | 1910.0 [M + H]$^{+}$ |
| phosphorylated pKID-Abl | Ac-DKDADGWEAIpYAAPFAK-NH$_2$ | 1988.1 | 1990.4 [M + H]$^{+}$ |
| non-phosphorylated pKID-pTyr12 | Ac-DKNADGWIDAAYK-NH$_2$ | 1507.6 | 1509.2 [M + 2H]$^{2+}$ |
| phosphorylated pKID-pTyr12 | Ac-DKNADGWIDAApYK-NH$_2$ | 1586.1 | 1587.6 [M + H]$^{+}$ |
| EF Control-E11 | Ac-DKNADGWIDAEAK-NH$_2$ | 1473.5 | 1475.2 [M + 2H]$^{2+}$ |
| EF Hand-E12 | Ac-DKNADGWIDAAEK-NH$_2$ | 1473.5 | 1471.5 [M − H]$^{-}$ | pY indicates phosphotyrosine. Observed masses of peptides for which the multiply charged species were detected are reported as the deconvoluted masses.

Luminescence Experiments

All experiments were conducted on a Photon Technology International fluorescence spectrometer model QM-3/2003 with a CW source and a Hamamatsu R928PMT using 10 nm excitation and emission slit widths. A 495 nm highpass filter (model 495FG03-25 AM-53074; Andover Corporation) was used on the emission monochromator. Spectra were acquired at room temperature with a scan rate of 1 nm per second. In dissociation constant determinations, the observed luminescence (photon counts s$^{-1}$) was not background-corrected and represents the raw fluorescence data. In the presence of buffer only (no peptide, no metal), the luminescence at 544 nm is similar to the luminescence observed in the presence of peptide at the limit of low concentrations of Tb$^{3+}$ (approximately 1.8×10$^5$ photon counts s$^{-1}$). Spectral data (FIGS. 3a, 3c, and 3d) represent the average of at least three independent trials and correspond to the averaged spectra that yielded the data points at the given Tb$^{3+}$ concentrations in the dissociation constant determination plots. Spectral data in the manuscript were background-corrected. Peptide solutions were prepared by the dilution of peptide stock solutions into buffer containing 5 mM HEPES (pH 7.8) and 100 mM NaCl (final concentrations). Spectra were acquired in 10 mm quartz fluorescence cells (Starna). Tb$^{3+}$ titrations were conducted by dilution of a Tb$^{3+}$ solution into a peptide solution. All TbCl$_3$ solutions were standardized by titration with a standard solution of EDTA (1 mM) in the presence of xylenol orange indicator (10 µM) and sodium acetate buffer (pH 6.0, 10 mM). EDTA (1 mM) was added to 500 µL of a 1 mM Tb$^{3+}$ solution diluted from a 10 mM stock until the end point was reached; Tb$^{3+}$ concentration was determined based on 1:1 binding. Each individual emission spectrum represents an independently prepared solution of peptide and metal. The Tb$^{3+}$ emission band at 544 nm was used to evaluate metal binding.

Dissociation Constant Determination

To determine dissociation constants for Tb$^{3+}$-peptide complexes, Tb$^{3+}$ titrations were conducted in solutions of 5 mM HEPES (pH 7.8) and 100 mM NaCl. Each data point represents an independently prepared solution of peptide and metal. Observed luminescence (photon counts s$^{-1}$) at the emission maximum of 544 nm were plotted against Tb$^{3+}$ concentration to calculate the final K$_d$. Data points indicate the average of at least three independent titrations. Error bars indicate standard error. The data were fit to equation (1) using a non-linear least squares fitting algorithm (KaleidaGraph version 4.0, Synergy Software), where Q=luminescence, Q$_o$=luminescence of the apopeptide, Q$_c$=luminescence of peptide-metal complex, M$_t$=total metal concentration, K$_d$=dissociation constant and P$_t$=total peptide concentration (10 µM, 5 µM, or 2 µM, as indicated). The quadratic equation solution to the dissociation constant (equation 1) was employed to generate an accurate solution to the binding equilibrium under conditions when the dissociation constant, peptide concentration, and metal concentration may be similar. For phosphorylated pKID-pTyr11, the dissociation constant was also measured in the presence of 2 mM Mg$^{2+}$ and 100 µM Ca$^{2+}$ to study the effect of these metals on Tb$^{3+}$-peptide complex formation.

$$Q = Q_o + (Q_c - Q_o)\frac{\left[(M_t + K_d + P_t) - \sqrt{(M_t + P_t + K_d)^2 - 4(P_t M_t)}\right]}{2P_t} \quad (1)$$

TABLE 3

Dissociation constants of peptide-$Tb^{3+}$ complexes in aqueous solutions of 5 mM HEPES (pH 7.8) and 100 mM NaCl.

| Peptide | Sequence | $K_d$, µM | Standard Error |
|---|---|---|---|
| Non-phosphorylated pKID-pTyr11 | Ac-DKNADGWIDAYAK-$NH_2$ | 1900 | 280 |
| 10 µM phosphorylated pKID-pTyr11 | Ac-DKNADGWIDApYAK-$NH_2$ | 54 | 9 |
| 2 µM phosphorylated pKID-pTyr11 | | 32 | 5 |
| 2 µM phosphorylated pKID-pTyr11 with 2 mM $Mg^{2+}$ and 100 µM $Ca^{2+}$ | | 30 | 2 |
| non-phosphorylated pKID-pTyr15a | Ac-DKNADGWIDAAAAKYAK-$NH_2$ | $3200^a$ | $330^a$ |
| phosphorylated pKID-pTyr15a | Ac-DKNADGWIDAAAAKpYAK-$NH_2$ | 217 | 21 |
| non-phosphorylated pKID-pTyr15b | Ac-DKDGDGWISPAAAKYAK-$NH_2$ | $1930^a$ | $100^a$ |
| phosphorylated pKID-pTyr15b | Ac-DKDGDGWISPAAAKpYAK-$NH_2$ | 47 | 5 |
| non-phosphorylated pKID-Abl | Ac-DKDADGWEAIYAAPFAK-$NH_2$ | 411 | 38 |
| phosphorylated pKID-Abl | Ac-DKDADGWEAIpYAAPFAK-$NH_2$ | 26 | 6 |
| non-phosphorylated pKID-pTyr12 | Ac-DKNADGWIDAAYK-$NH_2$ | 6470 | 630 |
| phosphorylated pKID-pTyr12 | Ac-DKNADGWIDAApYK-$NH_2$ | 209 | 32 |
| EF Control-E11 | Ac-DKNADGWIDAEAK-$NH_2$ | 1820 | 140 |
| EF Hand-E12 | Ac-DKNADGWIDAAEK-$NH_2$ | 88 | 8 | pY indicates phosphotyrosine. 10 µM peptide was used unless indicated otherwise.$^a$ In general, non-phosphorylated peptides bound $Tb^{3+}$ poorly and did not display evidence of saturation binding, precluding accurate determination of dissociation constants for these peptide-$Tb^{3+}$ complexes. Non-phosphorylated pKID-pTyr11 showed evidence of saturation, but the binding was extremely cooperative and suggestive of non-1:1 $Tb^{3+}$:peptide stoichiometry. Dissociation constants of the non-phosphorylated peptides indicated by $^a$ were calculated by defining the maximum luminescence of the non-phosphorylated peptide-$Tb^{3+}$ complex as equal to the maximum luminescence of the phosphorylated peptide-$Tb^{3+}$ complex: $Q_c$ (non-phosphorylated peptide)=$Q_c$ (phosphorylated peptide), with $Q_c$=the calculated luminescence of the fully bound phosphopeptide-$Tb^{3+}$ complex. Although the assumption of similar maximum luminescence intensities of the $Tb^{3+}$ complexes of the non-phosphorylated and phosphorylated peptides may not be valid, it provides a measure of the relative $Tb^{3+}$ luminescence of the phosphorylated and non-phosphorylated peptides.

Kinase Assays

Non-phosphorylated pKID-Abl (240 µM) was incubated with 300 units of Abl tyrosine kinase (New England Biolabs) in a 25 µL reaction containing 10 mM HEPES pH 7.5, 100 mM NaCl, 2 mM $Mg^{2+}$, 400 µM ATP, and 2 mM DTT for 30 min at 37° C. in the presence or absence of 50 µM Gleevec (Toronto Research Chemicals). The reaction was diluted with standard fluorescence assay buffer (see above) and $Tb^{3+}$ to give a 30 µM peptide solution. Fluorescence assays were performed as described above with the addition of 50 µM $Tb^{3+}$ (final concentration). Enzymes were heat-inactivated at 65° C. for 30 min prior to HPLC analysis. Analytical HPLC analysis of the reaction mixtures indicated 62% conversion of non-phosphorylated pKID-Abl to phosphorylated pKID-Abl in the absence of Gleevec, while less than 5% conversion was observed in the presence of Gleevec. Data (FIG. 4b) represent the average of three independent trials. Error bars indicate standard error.

Phosphatase Assays

An 80 µM solution of phosphorylated pKID-Abl was incubated with 20 units of Protein Tyrosine Phosphatase (YOP) (New England Biolabs) in the presence of 20 mM HEPES pH 7.5, 100 mM NaCl, and 5 mM DTT at 37° C. for 1 min. 25 µL of the reaction mixture at 0 and 1 min time points was diluted in 175 µL of fluorescence assay buffer to yield a 10 µM peptide solution with 20 µM $Tb^{3+}$ (final concentration). Enzymes were heat-inactivated at 65° C. for 30 min prior to HPLC analysis. Analytical HPLC analysis of the reaction mixtures after 1 min indicated>95% conversion of the phosphorylated peptide to the non-phosphorylated peptide. Data (FIG. 4c) represent the average of three independent trials. Error bars indicate standard error.

Cell Extract Kinase Assays

Cell extracts were prepared from $3\times10^8$ HeLa cells. HeLa cells were cultured in Dulbecco's Modified Eagle Medium (DMEM) with 10% heat inactivated fetal bovine serum, penicillin (100 units/mL), and streptomycin (100 µg/mL) in a 37° C. humidified environment containing 5% $CO_2$. Serum starvation was achieved by incubation in DMEM containing 0.5% heat-inactivated fetal bovine serum for 20 hours prior to the direct addition of Epidermal Growth Factor (EGF) (100 ng/mL) into this medium. The Epidermal Growth Factor stimulation was allowed to proceed for 10 min. Cells were then trypsinized and spun down, followed by resuspension in 2 mL of PBS (8 mM $Na_3PO_4$, 1.5 mM $K_3PO_4$, 2.7 mM KCl and 137 mM NaCl in high purity $dH_2O$, pH 7.4). The cells were spun down and resuspended in 1 mL of Buffer C (0.4 M HEPES (pH 7.9), 60 mM $MgCl_2$, 400 mM KCl, 20 mM DTT, 8 mM phenylmethylsulfonyl fluoride (PMSF) in $dH_2O$). The cells were spun down and resuspended again in 1 mL Buffer C and set on ice for 10 min. Upon lysis, the cells were vortexed for 30 seconds, spun down, and resuspended in 1 mL Buffer D (100 mM HEPES (pH 7.9), 4.1 M NaCl, 14.7 mM $MgCl_2$, 200 μM EDTA, 5 mM dithiothreitol (DTT), 5 mM PMSF in 2.5% glycerol), set on ice for 15 min, then spun down. The supernatant was aliquoted and frozen.

pKID-Abl Phosphorylation in HeLa Cell Extracts.

Reaction mixtures were prepared to a final volume of 100 μL as follows: stock solutions were mixed to yield final concentrations of 200 μM ATP, 200 μM β-glycerolphosphate, 200 μM sodium orthovanadate ($Na_3VO_4$), 2 mM DTT, and 200 μM non-phosphorylated pKID-Abl using 70 μL of untreated or EGF-treated HeLa cell extracts. The cell extract solutions were incubated at 37° C. and supplemented with 100 μM ATP every 1 hour. After 10 hours, the reaction mixture was analyzed by HPLC, fluorescence, and ESI-MS. Before fluorescence and HPLC analysis, the reaction mixtures were sonicated for 30 seconds using an ultrasonicator (Fisher Scientific, FS20). Fluorescence samples were prepared by adding 100 μL $TbCl_3$ solution (700 μM) directly to the reaction mixtures. Data (FIG. 4d) represent the average of three independent trials. Error bars indicate standard error.

Circular Dichroism

Circular dichroism spectra were collected at 277 K on an Aviv model 62DS circular dichroism spectropolarimeter in a 1 mm cell with 50 μM peptide in 5 mM HEPES buffer (pH 7.8) containing 10 mM NaCl in the presence or absence of 100 μM. $Tb^{3+}$. Data represent the average of three independent trials. Data were background-corrected and were smoothed using a 3 point window. Individual spectra were collected every nm with a bandwidth of 2 nm and an averaging time of 4 s. Samples were allowed to thermally equilibrate for 5 min prior to data collection.

NMR Spectroscopy

Phosphorylated pKID-pTyr11 (580 μM final concentration) was dissolved in 90% $H_2O$/10% $D_2O$ containing 10 mM NaCl and the pH of the solution adjusted to pH 6.0. Spectra were collected on the sample in the absence and in the presence of 600 μM $La^{3+}$ (1.03 equivalent). NMR spectra were collected at 23° C. on a Brüker AVC 600 MHz NMR spectrometer equipped with a TXI triple resonance probe. Spectra were internally referenced with deuterated 3-trimethylsilyl-proprionate (100 μM). TOCSY and NOESY spectra were collected with water suppression using a gradient watergate pulse sequence (Brüker pulse sequences mlevgpph19 and noesygpph19, respectively). TOCSY spectra were acquired with sweep widths of 7183 Hz in $t_1$ and $t_2$, 800×4096 complex data points, 8 scans per $t_1$ increment, a relaxation delay of 1.8 s, and a TOCSY mixing time of 60 ms. NOESY spectra were acquired with sweep widths of 7183 Hz in $t_1$ and $t_2$, 800×2048 complex data points, 16 scans per $t_1$ increment, a relaxation delay of 1.8 s, and a NOESY mixing time of 300 ms. Residues were assigned via TOCSY and NOESY spectra, with sequential residues identified via NOEs between $H_\alpha(i)$ and $H_N(i+1)$.

TABLE 4

Resonance assignments of phosphorylated pKID-pTyr11 in the absence of metal.

| residue | $\delta, H^N$ | $\delta, H_\alpha$ | $\delta, H_\beta$ | $H_{other}$ |
|---|---|---|---|---|
| Asp1 | 8.26 | 4.54 | 2.69, 2.58 | |
| Lys2 | 8.36 | 4.16 | 1.73 | 2.94, 1.68, 1.61, 1.30 |
| Asn3 | 8.44 | 4.66 | 2.81, 2.80 | 7.63, 6.90 |
| Ala4 | 8.22 | 4.29 | 1.41 | |
| Asp5 | 8.30 | 4.57 | 2.67, 2.62 | |
| Gly6 | 8.33 | 3.98, 3.89 | | |
| Trp7 | 7.99 | 4.59 | 3.28, 3.28 | 10.17, 7.59, 7.50, 7.23, 7.14 |
| Ile8 | 7.73 | 3.96 | 1.65 | 1.34, 1.01, 0.78 |
| Asp9 | 8.12 | 4.39 | 2.71, 2.56 | |
| Ala10 | 8.23 | 4.14 | 1.28 | |
| pTyr11 | 8.20 | 4.47 | 3.09, 3.02 | 7.19, 7.12 |
| Ala12 | 7.91 | 4.23 | 1.37 | |
| Lys13 | 8.06 | 4.20 | 1.84 | 2.98, 1.74, 1.69, 1.43 |
| Ac- | | 2.02 | | |
| —$NH_2$ | | | | 7.59, 7.50 |

TABLE 5

Resonance assignments of phosphorylated pKID-pTyr11 in the presence of $La^{3+}$.

| residue | $\delta, H^N$ | $\delta, H_\alpha$ | $\delta, H_\beta$ | $H_{other}$ |
|---|---|---|---|---|
| Asp1 | 8.32 | 4.60 | 2.72, 2.61 | |
| Lys2 | 8.57 | 4.23 | 1.79 | 2.96, 1.64, 1.42 |
| Asn3 | 8.48 | 4.73 | 2.84 | 7.77, 7.02 |
| Ala4 | 8.25 | 4.25 | 1.39 | |
| Asp5 | 8.28 | 4.61 | 2.74, 2.68 | |
| Gly6 | 8.38 | 3.96, 3.82 | | |
| Trp7 | 8,07 | 4.69 | 3.26, 3.26 | 10.14, 7.62, 7.50, 7.22, 7.15 |
| Ile8 | 7.98 | 4.00 | 1.69 | 1.34, 1.01, 0.80 |
| Asp9 | 8.33 | 4.47 | 2.62, 2.52 | |
| Ala10 | 8.18 | 4.23 | 1.27 | |
| pTyr11 | 8.05 | 4.54 | 3.15, 2.95 | 7.21, 7.16 |
| Ala12 | 8.10 | 4.29 | 1.38 | |
| Lys13 | 8.19 | 4.24 | 1.86 | 2.99, 1.77, 1.69, 1.45 |
| Ac- | | 2.02 | | |
| —$NH_2$ | | | | 7.54, 7.14 |

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

REFERENCES

1. Manning, G.; Whyte, D. B.; Martinez, R.; Hunter, T.; Sudarsanam, S. *Science* 2002, 298, 1912-1934.
2. Tibes, R.; Trent, J.; Kurzrock, R. *Ann. Rev. Pharmacol. Toxicol.* 2005, 45, 357-384.
3. Rothman, D. M.; Shults, M. D.; Imperiali, B. *Trends Cell Biol.* 2005, 15, 502-510.
4. Lawrence, D. S.; Wang, Q. *ChemBioChem* 2007, 8, 373-378.
5. Ting, A. Y.; Kain, K. H.; Klemke, R. L.; Tsien, R. Y. *Proc. Natl. Acad. Sci. USA* 2001, 98, 15003-15008.
6. Kurokawa, K.; Mochizuki, N.; Ohba, Y.; Mizuno, H.; Miyawaki, A.; Matsuda, M. *J. Biol. Chem.* 2001, 276, 31305-31310.
7. Sato, M.; Ozawa, T.; Inukai, K.; Asano, T.; Umezawa, Y. *Nat. Biotechnol.* 2002, 20, 287-294.

8. Kawai, Y.; Sato, M.; Umezawa, Y. *Anal. Chem.* 2004, 76, 6144-6149.
9. Hofmann, R. M.; Cotton, G. J.; Chang, E. J.; Vidal, E.; Veach, D.; Bornmann, W.; Muir, T. W. *Bioorg. Med. Chem. Lett.* 2001, 11, 3091-3094.
10. Ojida, A.; Mito-oka, Y.; Inoue, M.; Hamachi, I. *J. Am. Chem. Soc.* 2002, 124, 6256-6258.
11. Shults, M. D.; Imperiali, B. *J. Am. Chem. Soc.* 2003, 125, 14248-14249.
12. Ojida, A.; Mito-oka, Y.; Sada, K.; Hamachi, I. *J. Am. Chem. Soc.* 2004, 126, 2454-2463.
13. Wang, Q. Lawrence, D. S. *J. Am. Chem. Soc.* 2005, 127, 7684-7685.
14. Shults, M. D.; Janes, K. A.; Lauffenburger, D. A.; Imperiali, B. *Nature Methods* 2005, 2, 277-283.
15. Wang, Q.; Cahill, S. M.; Blumenstein, M.; Lawrence, D. S. *J. Am. Chem. Soc.* 2006, 128, 1808-1809.
16. Sahoo, H.; Hennig, A.; Florea, M.; Roth, D.; Enderle, T.; Nau, W. M. *J. Am. Chem. Soc.* 2007, 129, 15927-15934.
17. Lukovic, E.; Gonzalez-Vera, J. A.; Imperiali, B. *J. Am. Chem. Soc.* 2008, 130, 12821-12827.
18. Green, K. D.; Pflum, M. K. H. *ChemBioChem* 2009, 10, 234-237.
19. Szilak, L.; Moitra, J.; Krylov, D.; Vinson, C. *Nature Struct. Biol.* 1997, 4, 112-114.
20. Szilak, L.; Moitra, J.; Vinson, C. *Protein Sci.* 1997, 6, 1273-1283.
21. Signarvic, R. S.; DeGrado, W. F. *J. Mol. Biol.* 2003, 334, 1-12.
22. Errington, N.; Doig, A. J. *Biochemistry* 2005, 44, 7553-7558.
23. Balakrishnan, S.; Zondlo, N. J. *J. Am. Chem. Soc.* 2006, 128, 5590-5591.
24. Riemen, A. J.; Waters, M. L. *J. Am. Chem. Soc.* 2009, 131, 14081-14087.
25. Ambroggio, X. I.; Kuhlman, B. *Curr. Opin. Struct. Biol.* 2006, 16, 525-530.
26. Atkinson, P.; Bretonniere, Y.; Parker, D. *Chem. Comm.* 2004, 438-439.
27. Atkinson, P.; Murray, B. S.; Parker, D. *Org. Biomol. Chem.* 2006, 4, 3166-3171.
28. Tremblay, M. S.; Zhu, Q.; Marti, A. A.; Dyer, J.; Halim, M.; Jockusch, S.; Turro, N. J.; Sames, D. *Org. Lett.* 2006, 8, 2723-2726.
29. Tremblay, M. S.; Lee, M.; Sames, D. *Org. Lett.* 2008, 10, 5-8.
30. Liu, L. L.; Franz, K. J. *J. Am. Chem. Soc.* 2005, 127, 9662-9663.
31. Liu, L. L.; Franz, K. J. *J. Biol. Inorg. Chem.* 2007, 12, 234-247.
32. Chattopadhyaya, R.; Meador, W. E.; Means, A. R.; Quiocho, F. A. *J. Mol. Biol.* 1992, 228, 1177-1192.
33. Siedlecka, M.; Goch, G.; Ejchart, A.; Sticht, H.; Bierzynski, A. *Proc. Natl. Acad. Sci. USA* 1999, 96, 903-908.
34. Kraulis, P. J. *J. Appl. Crystallogr.* 1991, 24, 946-950.
35. Macmanus, J. P.; Hogue, C. W.; Marsden, B. J.; Sikorska, M.; Szabo, A. G. *J. Biol. Chem.* 1990, 265, 10358-10366.
36. Nitz, M.; Franz, K. J.; Maglathlin, R. L.; Imperiali, B. *ChemBioChem* 2003, 4, 272-276.
37. Songyang, Z.; Carraway, K. L.; Eck, M. J.; Harrison, S. C.; Feldman, R. A.; Mohammadi, M.; Schlessinger, J.; Hubbard, S. R.; Smith, D. P.; Eng, C.; Lorenzo, M. J.; Ponder, B. A. J.; Mayer, B. J.; Cantley, L. C. *Nature* 1995, 373, 536-539.
38. Rychlewski, L.; Kschischo, M.; Dong, L.; Schutkowski, M.; Reimer, U. *J. Mol. Biol.* 2004, 336, 307-311.
39. Hutti, J. E.; Jarrell, E. T.; Chang, J. D.; Abbott, D. W.; Storz, P.; Toker, A.; Cantley, L. C.; Turk, B. E. *Nat. Methods* 2004, 1, 27-29.
40. Turk, B. E. *Curr. Opin. Chem. Biol.* 2008, 12, 4-10.
41. Placzek, E. A.; Plebanek, M. P.; Lipchik, A. M.; Kidd, S. R.; Parker, L. L. *Anal. Biochem.* 2010, 397, 73-78.
42. Nelson, M. R.; Chazin, W. J. *Biometals* 1998, 11, 297-318; Rigden, D. J.; Galperin, M. Y. *J. Mol. Biol.* 2004, 343, 971-984.
43. Aurora, R.; Rose, G. D. *Protein Sci.* 1998, 7, 21-38; Kemp, D. S.; Boyd, J. G.; Muendel, C. C. *Nature* 1991, 352, 451-454.
44. Tonks, N. K. *Nat. Rev. Mol. Cell. Biol.* 2006, 7, 833-846.
45. Ostman, A.; Hellberg, C.; Bohmer, F. D. *Nat. Rev. Cancer* 2006, 6, 307-320.
46. Vang, T.; Miletic, A. V.; Arimura, Y.; Tautz, L.; Rickert, R. C.; Mustelin, T. *Ann. Rev. Immunol.* 2008, 26, 29-55.
47. Krishnamurthy, D.; Barrios, A. M. *Curr. Opin. Chem. Biol.* 2009, 13, 375-381.
48. Blaskovich, M. A. T. *Curr. Med. Chem.* 2009, 16, 2095-2176.
49. Mitra, S.; Barrios, A. M. *Bioorg. Med. Chem. Lett.* 2005, 15, 5142-5145.
50. Mitra, S.; Barrios, A. M. *Anal. Biochem.* 2007, 370, 249-251.
51. Sculimbrene, B. R.; Imperiali, B. *J. Am. Chem. Soc.* 2006, 128, 7346-7352,
52. Eftink, M. R. *Methods Enzymol.* 1997, 278, 221-257.

What is claimed:

1. An isolated polypeptide comprising a tyrosine kinase-inducible domain (pKID), wherein the pKID comprises an amino acid sequence selected from the group consisting of
    (a) an amino acid sequence having formula (I):

$$DKX^1X^2DGWX^3x^4x^5x^6x^7x^8x^9x^{10} \quad (1)$$

wherein $X^1$ is D or N;
    $X^2$ is A or G;
    $X^3$, $X^4$ and $X^5$ are each an amino acid; and
    $X^6$ is Y while $X^7$, $X^8$, $X^9$ and $X^{10}$ are each an optionally present amino acid; and
    (b) an amino acid sequence of SEQ ID NO: 7, 8 or 10.

2. The isolated polypeptide of claim 1, wherein the pKID is phosphorylated.

3. The isolated polypeptide of claim 1, wherein the pKID comprises an amino acid sequence selected from the group consisting of SEQ ID NOs: 1-12.

* * * * *